United States Patent [19]

Clark et al.

[11] Patent Number: 5,059,210

[45] Date of Patent: Oct. 22, 1991

[54] APPARATUS AND METHODS FOR ATTACHING AND DETACHING AN ULTRASONIC ACTUATED BLADE/COUPLER AND AN ACOUSTICAL MOUNT THEREFOR

[75] Inventors: Richard J. Clark, Norfolk, Mass.; Alan E. Thomas, Ocean City, N.J.

[73] Assignee: Ultracision Inc., Smithfield, R.I.

[21] Appl. No.: 448,862

[22] Filed: Dec. 12, 1989

[51] Int. Cl.⁵ ............................................. A61F 5/04
[52] U.S. Cl. .................................. 606/169; 81/121.1; 464/37; 606/167
[58] Field of Search .................... 81/121.1, 124.3, 467, 81/472, 473, 474, 476, 477, 478, 440, 307, 309, 336, 337; 279/1 R; 29/242; 464/37, 38; 192/46, 56 R; 606/167-172

[56] References Cited

U.S. PATENT DOCUMENTS

| | | |
|---|---|---|
| 2,441,038 | 5/1948 | Sesel .................................... 464/37 |
| 2,797,564 | 7/1957 | Bonneau et al. ........................ 464/38 |
| 2,899,841 | 8/1959 | Melloy .................................. 192/46 |
| 2,916,117 | 12/1959 | Ondeck .............................. 192/56 R |
| 3,373,491 | 3/1968 | Montelius . |
| 3,597,582 | 8/1971 | Goode et al. . |
| 3,799,168 | 3/1974 | Peters . |
| 3,804,096 | 4/1974 | Gonser . |
| 3,964,163 | 6/1976 | Russo . |
| 4,014,343 | 3/1977 | Esty . |
| 4,093,210 | 6/1978 | Terpening ............................. 272/67 |
| 4,123,840 | 11/1978 | Rumer Jr. . |
| 4,130,271 | 12/1978 | Merriman ............................... 192/46 |
| 4,131,039 | 12/1978 | Garonnet ............................... 192/46 |
| 4,180,162 | 12/1979 | Magney . |
| 4,291,864 | 9/1981 | Reynolds ........................... 192/56 R |
| 4,359,052 | 11/1982 | Staub . |
| 4,674,498 | 6/1987 | Stasz . |
| 4,679,468 | 7/1987 | Gray .................................... 81/121.1 |
| 4,730,376 | 3/1988 | Yamada . |
| 4,735,202 | 4/1988 | Williams . |
| 4,754,754 | 7/1988 | Garito et al. . |
| 4,826,490 | 5/1989 | Byrne et al. . |
| 4,832,021 | 5/1989 | Kuhl et al. . |
| 4,846,025 | 7/1989 | Keller et al. ........................... 81/3.09 |

Primary Examiner—Richard J. Apley
Assistant Examiner—Linda C. M. Dvorak
Attorney, Agent, or Firm—Nixon & Vanderhye

[57] ABSTRACT

A delivery system for attaching and detaching an ultrasonic surgical blade/coupler and an acoustical mount. An adaptor sleeve receives and encapsulates the blade to avoid accidents resulting from the sharp blade edge. A cylindrical member receives the sleeve and a ratcheting mechanism is provided between the adaptor and member to facilitate rotation of the adaptor and coupler upon rotation of the member up to a predetermined torque, ensuring threaded connection between the coupler and acoustical mount sufficient for transmission of ultrasonic energy. To remove the blade/coupler, the member is rotated in the opposite direction, whereby unlimited torque may be applied through the ratchet mechanism to unthread the coupler from the mount.

19 Claims, 2 Drawing Sheets

APPARATUS AND METHODS FOR ATTACHING AND DETACHING AN ULTRASONIC ACTUATED BLADE/COUPLER AND AN ACOUSTICAL MOUNT THEREFOR

BACKGROUND AND SUMMARY OF THE INVENTION

The present invention relates generally to an ultrasonic surgical device delivery system and particularly relates to apparatus and methods for facilitating attachment and detachment of an ultrasonically-actuated blade/coupler assembly and an acoustical mount therefor.

Ultrasonic surgical devices for performing a variety of surgical procedures are well known. Generally, these surgical devices are hand-held instruments connected to a source of ultrasonic energy. The ultrasonic energy is transmitted through a connection or mount between the ultrasonic energy source and a hand-held coupler which mounts the surgical tool, for example, a surgical blade mounted at the tip of the hand-held coupler. Ultrasonic energy is therefore transmitted through the coupler to the surgical blade to facilitate a precise surgical incision.

Ultrasonic surgical devices, however, are not without problems when used. For example, an acoustically-actuated surgical device should be used in a sterile field. Ready attachment and detachment of the surgical device relative to the ultrasonic energy source is highly desirable. Traditionally, a screw-type mechanism has been employed to secure the ultrasonic surgical device to its acoustical mount so that the ultrasonic energy may be transmitted through the mount to the surgical device Because of the need for a sterile environment, the surgical device must be readily attached to the acoustical mount for use in a manner which maintains the sterile field. Quick detachment of the surgical device from its acoustical mount after use for sterilization or disposal is also highly desirable.

It will be appreciated that the connection between the surgical device and the ultrasonic energy source requires a tight union so that ultrasonic energy may be efficiently transmitted to the device at the desired power levels When a screwthread is used, the surgical device is often over-tightened to the acoustical mount by the surgeon, nurse or technician in order to ensure that ultrasonic energy is properly transmitted to the surgical device. Typically, this causes difficulties, not only when attaching the surgical device and its mount, but also when detaching the surgical device from the mount after use, i.e., it is often overtightened and therefore difficult to detach. Also, when attaching and detaching the surgical device and the acoustical mount, there is the obvious danger of injury to the doctor, nurse or technician as a result of contact with the surgical device itself, e.g., the blade. Additionally, it is very difficult for surgeons, nurses or technicians to connect and disconnect the surgical device and its acoustical mount in a sterile field using typical fastening devices such as pliers, wrenches and the like and without causing injury.

According to the present invention, there is provided an ultrasonic surgical device delivery system that overcomes the foregoing and other problems associated with the attachment and detachment of an ultrasonic surgical device and its acoustical mount and provides apparatus and methods facilitating attachment and detachment of an ultrasonic surgical device and an acoustical mount therefor affording various advantages in construction, operation and use in comparison with traditional prior systems. Particularly, the present invention, in a preferred embodiment thereof, provides an adaptor having a generally cylindrical sleeve and a radial flange at one end, the flange having a conical surface for directing the surgical device into the sleeve. The surgical device may, for example, include a blade/coupler having a surgical blade at one end and an internally threaded female connection at its opposite end for connection to the acoustical mount. Flats are provided along both the coupler of the surgical device and the interior of the adaptor sleeve whereby, when the adaptor receives the blade/coupler, the adaptor and coupler may be rotated as a unit. Preferably, the rearwardly facing annular surface of the flange is provided with a plurality of cam surfaces which form part of a circular ratchet mechanism. The cam surfaces may, for example, comprise ramps in each quadrant of the rearwardly facing annular surface and which ramps terminate in end stops.

A cooperating cylindrical member having a radially extending end flange is received over the sleeve of the adaptor and is rotatable relative to the adaptor. The end flange of the cylindrical member preferably has a pair of cam followers, e.g., end projections, for engaging two of the cam surfaces along the rearwardly facing annular surface of the adaptor flange, the projections being provided at diametrically opposed locations. Additionally, the cylindrical member is provided with diametrically opposed, radially extending wings preferably extending from the end flange the full length of the member, such wings facilitating manual purchase of the member and its rotation relative to the adaptor. The wings are preferably circumferentially spaced 90° from the end projections. In this manner, the portions of the end flanges of the cylindrical member carrying the projections may resiliently flex in an axial rearward direction. The cylindrical member is received about the adaptor sleeve and secured against axial movement relative thereto by spring-biased fingers at the end of the adaptor sleeve remote from the adaptor flange.

Preferably, the blade/coupler, adaptor and cylindrical member are provided in a sterile package, in assembly or not, as desired. In use, the blade/coupler, adaptor and member are removed from their sterile packaging and, if not assembled, are assembled one to the other and to the blade/coupler. Particularly, the blade end of the blade/coupler surgical device is inserted into the adaptor sleeve, the conical end surface of the adaptor facilitating that insertion by guiding the blade into the sleeve. The blade/coupler is also rotationally aligned with the adaptor sleeve such that the flats on the coupler engage the flats within the bore of the sleeve. The interior edges of the conical surface engages stops carried by the blade/coupler limiting its axial movement into the adaptor. It will be appreciated that the blade is wholly received within the adaptor sleeve. Thus, the sleeve protects an individual against exposure to the blade during attachment or detachment of the device relative to the acoustical mount.

To attach the surgical device to the mount, the blade/coupler is threaded on the mount. When the coupler is loosely tightened to the mount, the wings on the cylindrical member are grasped and the member is rotated in the conventional screw-threading direction. The end projections on the member frictionally engage the cam surfaces, and consequently, the adaptor and member are rotatable as a unit to further tighten the blade/coupler to the acoustical mount. As the joint tightens and the resistance to further threading increases, the projections start to slide along the cam surfaces while continuing to apply torque to the adaptor and the coupler whereby the coupler is further tightened. Particularly, the end projections move up the ramps, causing the flange carrying the projections to resiliently flex or yield in an axial rearward direction and hence cause greater frictional engagement between the end projections and the cam surfaces. At a predetermined torque, the projections will move past the high points or trailing ends of the cam surfaces and spring back to engage the leading portions of the next cam surfaces. Thus, upon rotating the member further, a ratcheting action is provided at a predetermined torque value between the cylindrical member and the adaptor. In this manner, the individual attaching the blade/coupler to the acoustical mount will recognize that sufficient torque has been applied to the blade/coupler to ensure its connection with the acoustical mount in such manner that the ultrasonic energy will be efficiently transferred to the surgical device and this will be accomplished without over-tightening the connection. The adaptor and member are then removed from the blade/coupler assembly and the ultrasonic surgical device is ready for use.

To detach the surgical device from the acoustical mount after use, the adaptor and member are applied to the blade end of the device similarly as previously described. The cylindrical member, however, is rotated in the opposite direction, i.e., in a direction to unthread the blade/coupler from the acoustical mount. The projections on the member will thus engage the end stops of the cam surfaces and rotate the adaptor and coupler to provide the necessary unthreading action. Essentially unlimited torque may be applied to the member when rotated in the unthreading direction. Importantly, the unthreading action is provided with the blade completely encapsulated within the sleeve of the adaptor, thus protecting the individual removing the surgical device from its mount from cuts and puncture wounds. Once removed, the entire blade/coupler, adaptor and cylindrical member assembly may be thrown away. Alternatively, the adaptor and member sub-assembly may be removed from the blade/coupler, whereby the latter may be sterilized for reuse.

With the foregoing features in mind, it will be readily seen that there are significant advantages and benefits afforded by the system of the present invention. For example, the surgical blade during attachment and detachment from the acoustical mount is completely encapsulated within the sleeve of the adaptor, thereby preventing injury to the individual performing those tasks. Additionally, the blade/coupler, together with the attaching and detaching mechanism, may be provided is part of a sterile package for single use and disposal. Further, the ratcheting action during attachment ensures that sufficient torque has been applied to the coupler so that the requisite ultrasonic energy will be efficiently transmitted from the ultrasonic source to the surgical device. Further tightening beyond the predetermined torque is thus not necessary and the problems associated with over-tightening are completely eliminated. The ratchet mechanism also signals the individual attaching the device to the mount that sufficient tightness has been achieved whereby over-tightening and difficult removal is prevented. Additionally, during removal, the same delivery system is used. The one-way ratchet also enables virtually unlimited torque to be applied to the coupler in the reverse unthreading direction to facilitate its removal from the acoustical mount. Further, when removed, the adaptor and member may remain attached to the blade/coupler throughout its disposal to provide a protective enclosure for the blade, thereby avoiding accidents resulting from the sharp edge of the blade and transmission of infectious diseases.

Accordingly, and in accordance with a preferred embodiment of the present invention, there is provided apparatus for attaching a surgical device to a mount wherein the surgical device includes a coupler carrying a surgical tool and wherein the apparatus comprises an adaptor including a sleeve for receiving the surgical tool, means carried by the adaptor and engageable with the coupler when the surgical tool is received by the adaptor for rotating the coupler upon rotation of the adaptor and means carried by the adaptor for rotating the adaptor to rotate the coupler. Also provided are means cooperable between the rotating means and the adaptor for limiting the torque applied by the adaptor to the coupler when the surgical tool is being attached to the mount.

In a further preferred embodiment according to the present invention, there is provided a method for attaching a surgical device to a mount wherein the surgical device includes a coupler carrying the surgical tool comprising the steps of providing an adaptor having a sleeve containing the surgical tool and engageable with the coupler such that the coupler may be rotated upon rotation of the adaptor, providing a rotatable member carried by the adaptor, rotating the member to rotate the adaptor and coupler, and limiting the torque applied by the adaptor to the coupler in response to rotation of the member in one direction.

Accordingly, it is a primary object of the present invention to provide novel and improved apparatus and methods for attaching and detaching a surgical device relative to its energy source.

These and further objects and advantages of the present invention will become more apparent upon reference to the following specification, appended claims and drawings.

BRIEF DESCRIPTION OF THE DRAWINGS FIGURES

DETAILED DESCRIPTION OF THE DRAWING FIGURES

Reference will now be made in detail to the present preferred embodiment of the invention, an example of which is illustrated in the accompanying drawings.

Figure 1:
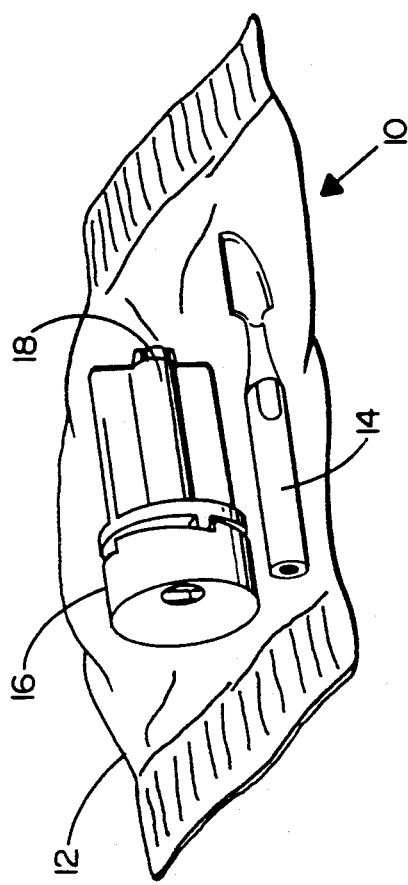
FIG. 1 is a perspective illustration of an ultrasonic surgical device delivery system constructed according to the present invention and illustrated within a sterile package.

Referring now to the drawings, there is illustrated in FIG. 1 an ultrasonic surgical device delivery system constructed according to the present invention and generally designated 10. The system is illustrated encapsulated within a sterile, preferably plastic, package 12. The general parts of the delivery system 10 include a surgical device, e.g., a blade/coupler 14, an adaptor 16 and a cylindrical member 18. The adaptor 16 and cylindrical member 18 are shown in assembly within the package 12, while the blade/coupler 14 is illustrated as a separate part. It will be appreciated that the system may include within the sterile package 12 a complete assembly of its component parts, that is, the blade/coupler 14 may be disposed within the adaptor 16 with the member 18 assembled thereon, as will be apparent to those skilled in this art. Alternately, the component parts may be provided separately within the packaging 12 and assembled at the time of use.

Figure 2:
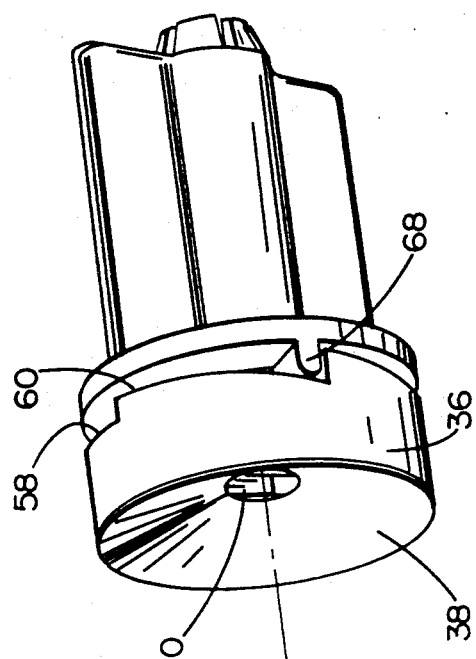
FIG. 2 is a schematic fragmentary perspective view illustrating the cooperation of the various parts of the delivery system hereof in use.
Figure 2:
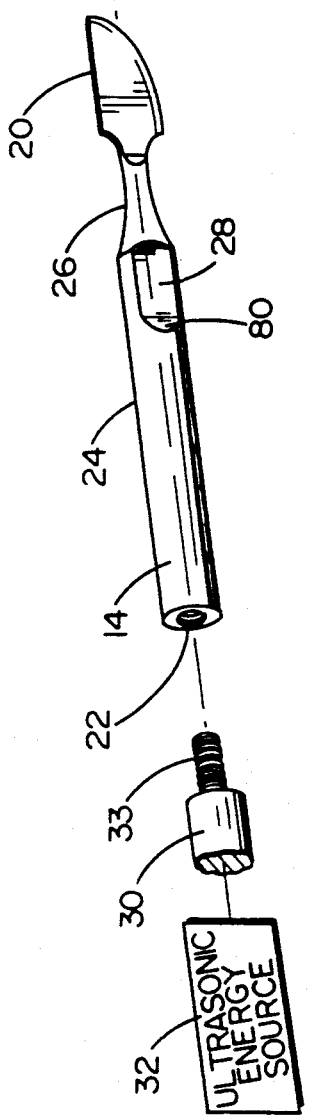

Referring now to FIG. 2, the blade/coupler 14 mounts a surgical tool 20, for example, a blade, at one end and has an internally threaded female bore 22 at its opposite end. The body 24 of blade/coupler 14 comprises a generally cylindrical member having a tapered head portion 26 terminating in blade 20. Diametrically opposed flats 28 are provided along the opposite sides of the body member 24 for reasons which will become clear. Blade/coupler 14 is adapted for threaded engagement with an acoustical mount 30 which is coupled to an ultrasonic energy source 32, whereby ultrasonic energy may be provided blade 20 for precision cutting. To effect the transmission of the ultrasonic energy, the blade/coupler 14 is screw-threaded to mount 30, the latter having an externally threaded male projection 33 for reception in the internally threaded female bore 22.

Figure 3:
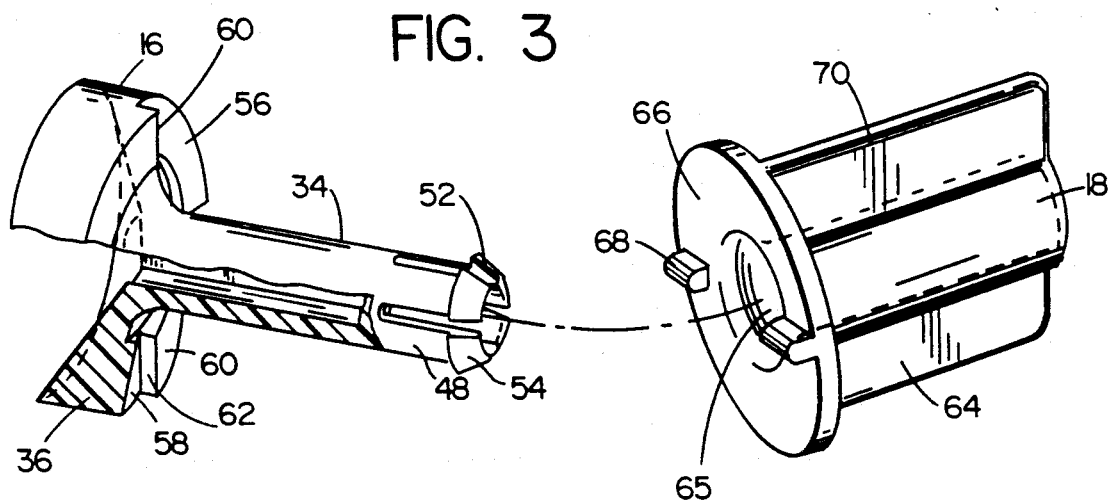
FIG. 3 is a fragmentary perspective view with parts broken out and in cross-section illustrating the cooperation between the adaptor and the cylindrical member.
Figure 4:
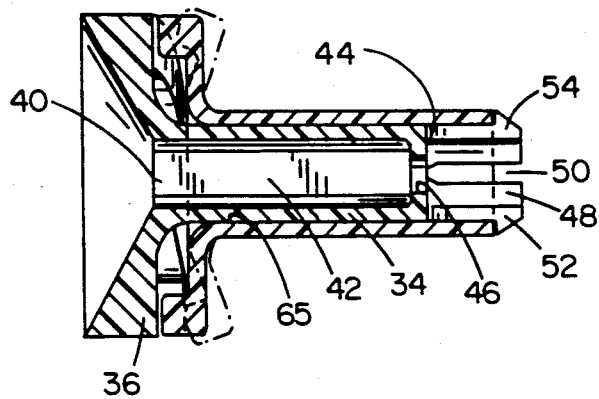
FIG. 4 is a cross-sectional view through the assemblage of the adaptor and cylindrical member illustrating the cooperation of the end projections on the cam surfaces of the member and adaptor, respectively.
Figure 5:
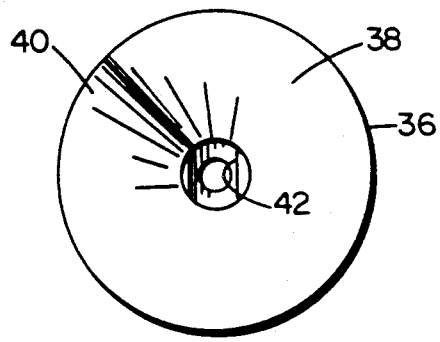
FIG. 5 is an end elevational view of the adaptor.

Turning now to FIGS. 3-5, adaptor 16 may comprise a generally cylindrical sleeve 34 terminating at one end in an enlarged radially extending flange 36. As illustrated in FIG. 2, the end face of flange 36 comprises a frustoconical surface 38 for guiding blade 20 into the bore 40 within sleeve 34. Bore 40 is provided with a pair of diametrically opposed flats 42 for registration and alignment with flats 28 on the opposite sides of blade/coupler 14 upon full insertion of blade/coupler 14 into adaptor sleeve 34, in a manner described in detail hereinafter.

The end of sleeve 34 opposite flange 36 includes an inwardly directed radial flange or end surface 44 having a reduced diameter bore opening 46 and a plurality of circumferentially spaced, axially extending, resiliently flexible fingers 48, spaced one from the other by axially extending slots 50. Each finger 48 terminates at its distal end in a radially outwardly projecting locking tip 52 having a tapered camming surface 54.

As best illustrated in FIGS. 2 and 3, the proximal face of flange 36, that is, the face of flange 36 closer to the user, is provided with a plurality of cam surfaces 56 at circumferentially spaced positions thereabout forming part of a ratchet mechanism. For example, cam surfaces 56 may comprise ramps, four being illustrated, and which ramps extend from low points 58 to high points 60. Each high point terminates in an axially extending end face or stop 62 at the beginning of the low point 58 of the circumferentially adjacent ramp 56.

Referring to FIGS. 2-4, cylindrical member 18 comprises a sleeve 64 having an internal bore 65 for snugly receiving sleeve 34 of adaptor 16. At one end of cylindrical member 18, there is provided a radially outwardly extending flange 66 having a pair of cam followers, e.g., a pair of diametrically opposed axially extending projections 68. Extending proximally from flange 66 and projecting radially outwardly from sleeve 64 are a pair of diametrically opposed wings 70 which extend the full length of member 18. From a review of FIG. 3, it will be appreciated that wings 70 are circumferentially spaced from the circumferential locations of projections 68. For example, wings 70 are spaced 90° from each of projections 68. This enables a resilient flexing (FIG. 4) of the flange 66 at each of the points of engagement of projections 68 with cam surfaces 56, in a manner to be described. Wings 70 are used to facilitate manual purchase of the cylindrical member and rotation thereof relative to adaptor 16.

In use, the delivery system is removed from the sterile package 12 in a sterile field and the blade/coupler 14 is loosely screw-threaded to the acoustical mount 30. If the blade/coupler 14 is provided in the sterile package in assembly with the adaptor 16 and member 18, then the entire assembly is loosely screw-threaded to mount 30. If not, blade/coupler 14 may be separately loosely screw-threaded to mount 30. Adaptor 16 and member 18 may be assembled one with the other (if not previously provided in assembly in sterile package 12) by inserting sleeve 34 into bore 65 of sleeve 64 of member 18. It will be appreciated that, upon receiving sleeve 34, member 18 cams the locking tips 52 radially inwardly until the opposite end of member 18 clears the locking tips, at which time the fingers 48 resilient spring back to the position illustrated in FIG. 4, locking member 18 on adaptor 16. The relative dimensions of adaptor 16 and member 18 are such that the locking action occurs only when projections 68 bear against the lower ends, i.e., leading edges 58 of the ramps 56, whereby member 18 is prevented from axial movement along adaptor 16. Blade/coupler 14 is then inserted into the sub-assembly of adaptor 16 and member 18 by inserting blade 20 into bore 40 of sleeve 34 such that flats 28 are aligned with flats 42 within the bore. The end edges of the bore adjacent the conical surface 38 engage the distally extending radial enlargements 80 (FIG. 2) at the rear end of flats 28 to limit the extent to which the blade/coupler 14 is inserted into sleeve 34.

It will be appreciated that, with flats 28 and 42 aligned and bearing against one another, the entire sub-assembly of adaptor 16 and member 18 may be rotated as a unit. That is, flats 42 constitute a first means carried by the adaptor and engageable with the coupler for rotating the coupler upon rotation of the adaptor. Also, member 18 constitutes a second means carried by adaptor 16 for rotating the adaptor to rotate the coupler. Thus, to tighten the threaded connection between the blade/coupler 14 and mount 30, wings 70 on the member 18 are grasped and rotated, causing the adaptor 16 and the blade/coupler 14 to rotate as a unit, hence tightening the threaded connection. The force transmission between member 18 and adaptor 16 is provided by the frictional engagement between projections 68 and ramps 56. As increased torque is applied and resistance to tightening increases, the projections 58 overcome their frictional resistance on ramps 56 and begin to slide along ramps 56. At a predetermined torque value, the projections 68 reach the ends or high point 60 of ramps 56 and slip past those end points onto the low points or leading edges of the circumferentially adjacent ramps. Upon continued rotation of member 18 about adaptor 16, a circumferential ratcheting action occurs, at which time the individual applying the torque recognizes that sufficient torque has been applied to ensure a sufficiently tight threaded connection between blade/coupler 14 and mount 30 whereby the ultrasonic energy may be efficiently transmitted to blade 20. The adaptor 16 and member 18 are then simply withdrawn from the blade/coupler 14, exposing the blade 20 for use. It will be appreciated that when the blade/coupler 14 is applied to mount 30, blade 20 resides wholly within sleeve 34 of adaptor 16. Consequently, the individual applying blade/coupler 14 to mount 30 is protected from accidents, e.g., cuts resulting from the sharp blade edge. Additionally, by utilizing the ratcheting action, the predetermined torque necessary to screw-thread blade/coupler 14 to the transmission element 30 is not be exceeded. This prevents over-tightening and consequent difficulties in removing blade/coupler 14 from mount 30.

To remove blade/coupler 14 from mount 30, the individual grasps wings 70 of member 18 and rotates member 18 in the opposite or unthreading direction. It will be appreciated that the projections 68, upon rotation in the opposite direction, will engage against end stops 62. At this time, virtually unlimited torque may be applied to member 18 and which torque is transmitted through the cooperating projections 68, end stops 62 and flats 28 and 42 to unthread blade/coupler 14 from mount 30. Again, blade 20 is wholly encapsulated within the sleeve 34 during this unthreading action, thereby protecting the individual from accidents resulting from the sharp edge of the blade. Upon removing blade/coupler 14 from mount 30, the entire assembly, including blade/coupler 14, adaptor 16 and member 18, may then be thrown away. Alternatively, if blade/coupler 14 is non-disposable, it can be removed from the sub-assembly of adaptor 16 and member 18 for subsequent sterilization and re-use.

Preferably, adaptor 16 is formed of a polycarbonate, for example, Lexan®, while the member 18 may be formed of a polypropylene. By using such materials, it will be appreciated that flange 66 of member 18 is to a degree resilient. Thus, when member 18 is rotated relative to adaptor 16, with projections 68 riding upwardly on ramps 56, the flange will flex rearwardly i.e., in the proximal direction, as indicated by the dashed lines in FIG. 4.

Consequently, it will be appreciated that the objects of the present invention are fully met in the above-described preferred embodiment of the invention. Particularly, blade/coupler 14 may be applied to the acoustical mount 30 without the danger of accidents e.g., resulting from cuts caused by the sharp blade edge, and without over-tightening the connection, which would otherwise render disconnection of the blade/coupler 14 from mount 30 very difficult. That is, the tightening action is provided up to a predetermined torque and application of further torque results in a simple ratcheting action, without higher torque being applied to the threaded connection. Additionally, the same elements used to apply the blade/coupler 14 to mount 30 are used in the same manner to unthread blade/coupler 14 from mount 30. Unlimited torque, however, may be applied to the adaptor/member sub-assembly during unthreading, whereby any further tightening of the threaded connection through use of the device can be overcome. The delivery system is also provided in an inexpensive throw-away assembly whereby the assembly may be provided in a sterile environment and disposed of after use.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. Apparatus for attaching a surgical device to a mount wherein the surgical device includes a coupler carrying a surgical tool comprising:

an adaptor including a sleeve for receiving the surgical tool;

first means carried by said adaptor and engageable with the coupler when the surgical tool is received by the adaptor for rotating the coupler upon rotation of said adaptor;

second means carried by said adaptor for rotating said adaptor to rotate the coupler;

means cooperable between said second rotating means and said adaptor, and responsive to rotation of said second rotating means in one rotary direction, for limiting the torque applied by said adaptor to the coupler to a predetermined magnitude thereof when the surgical tool is being attached to the mount; and means cooperable between said second rotating means and said adaptor, and responsive to rotation of said second rotating means in the opposite rotary direction, for applying substantially unlimited torque to the adaptor and coupler including in excess of said predetermined torque, said second rotating means including a generally cylindrical member disposed on said sleeve, said torque-limiting means including a cam surface carried by one of said adaptor and said cylindrical member and a cam follower carried by the other of said adaptor and said cylindrical member and engageable with said cam surface, said cam follower and said cam surface being cooperable in response to rotation of said cylindrical member to rotate said adaptor and apply a torque thereto, said adaptor further including a generally radially extending flange adjacent one end, one of said cam surface and said cam follower being carried by said flange on the side thereof from which said sleeve extends, said cylindrical member carrying the other of said cam surface and said cam follower on an end thereof for axial engagement with said one of said cam surface and said cam follower on said flange.

2. Apparatus according to claim 1 wherein said first means includes a bore in said sleeve and a pair of flats carried by said sleeve in part defining said bore for engaging flats on the coupler.

3. Apparatus according to claim 1 wherein said second rotating means includes a generally cylindrical member disposed on said sleeve, said cylindrical member having at least one generally radially extending element for facilitating manual purchase of said cylindrical member and rotation thereof about said sleeve.

4. Apparatus according to claim 1 wherein said cam surface has a predetermined extent, said cam surface and said cam follower being engageable to rotate said adaptor in response to rotation of said cylindrical member and being relatively slidable such that said cam surface and said cam follower disengage one from the other in response to a predetermined torque applied to said adaptor and relative slidable engagement thereof a distance no greater than said predetermined extent.

5. Apparatus according to claim 1 wherein one of said cam surface and said cam follower is formed of a resilient material.

6. Apparatus according to claim 3 including means for retaining said cylindrical member on said sleeve.

7. Apparatus according to claim 3 wherein said sleeve has a coaxial bore and a pair of flats carried thereby within said bore for engaging flats on the coupler, said cylindrical member including at least one element extending radially therefrom to facilitate manual purchase of said member and rotation thereof about said sleeve.

8. Apparatus according to claim 1 in combination with said surgical device, said adaptor having a generally conical surface configured to guide said surgical tool into said sleeve.

9. Apparatus according to claim 1 wherein said cylindrical member has at least one generally radially extending element to facilitate manual purchase of said cylindrical member and rotation thereof about said sleeve, said cam surface having a predetermined extent terminating at an end stop, said cam surface and said cam follower being engageable to rotate said adaptor in response to rotation of said cylindrical member and being relatively slidable such that said cam surface and said cam follower disengage one from the other in response to a predetermined torque applied to said adaptor and relative slidable engagement thereof a distance about said predetermined extent, said resilient member being engageable with said stop in response to relative rotation of said adaptor and said cylindrical member in the opposite direction to facilitate removal of the surgical tool from the mount.

10. Apparatus according to claim 1 wherein said cam surface comprise a plurality of circumferentially spaced and extending ramps and said cam follower includes at least a projection for engaging along one of said ramps.

11. Apparatus according to claim 1 wherein said adaptor and said second means are formed solely of plastic material thereby facilitating their one-time disposable use.

12. Apparatus according to claim 1 wherein said flange is resilient and yieldable in an axial direction when said cam surface and said cam follower engage one another in an axial direction, said flange being formed of a resilient and yieldable plastic material for resilient yielding engagement thereof upon relative movement of a cam surface and cam follower.

13. Apparatus for attaching a surgical device to a mount wherein the surgical device includes a coupler carrying a surgical tool comprising:
an adaptor including a sleeve for receiving the surgical tool;
first means carried by said adaptor and engageable with the coupler when the surgical tool is received by the adaptor for rotating the coupler upon rotation of said adaptor;
second means carried by said adaptor for rotating said adaptor to rotate the coupler;
means cooperable between said second rotating means and said adaptor for limiting the torque applied by said adaptor to the coupler when the surgical tool is being attached to the mount;
said second rotating means including a generally cylindrical member disposed on said sleeve, said torque-limiting means including a cam surface carried by one of said adaptor and said cylindrical member and a cam follower carried by the other of said adaptor and said cylindrical member and engageable with said cam surface, said cam follower and said cam surface being cooperable in response to rotation of said cylindrical member to rotate said adaptor and apply a torque thereto;
said cam surface comprising a plurality of circumferentially spaced and extending ramps and said cam follower includes at least a projection for engaging along one of said ramps; and
said adaptor and said cylindrical member having respective radially extending flanges with faces thereof in axial opposition to one another, one of said flange faces carrying said ramps and the other of said flange faces carrying said projection whereby said projection is in sliding engagement with one of said ramps in response to relative rotation between said adaptor and said member.

14. Apparatus according to claim 13 wherein said cam follower includes a second projection along said other flange face circumferentially spaced from said first-mentioned projection through an angle of about 180° for engagement along another of said ramps.

15. Apparatus according to claim 13 wherein said adaptor and said second means are formed solely of plastic material thereby facilitating their one-time disposable use.

16. Apparatus for attaching a surgical device to a mount wherein the surgical device includes a coupler carrying a surgical tool comprising:
an adaptor including a sleeve for receiving the surgical tool;
first means carried by said adaptor and engageable with the coupler when the surgical tool is received by the adaptor for rotating the coupler upon rotation of said adaptor;
second means carried by said adaptor for rotating said adaptor to rotate the coupler; and
means cooperable between said second rotating means and said adaptor for limiting the torque applied by said adaptor to the coupler when the surgical tool is being attached to the mount;
said second rotating means including a generally cylindrical member disposed on said sleeve, said torque-limiting means including a cam surface carried by one of said adaptor and said cylindrical member and a cam follower carried by the other of said adaptor and said cylindrical member and engageable with said cam surface, said cam follower and said cam surface being cooperable in response to rotation of said cylindrical member to rotate said adaptor and apply a torque thereto; and
said adaptor and said cylindrical member having respective radially extending flanges with faces thereof in axial opposition to one another, said cam surface comprising a plurality of circumferentially spaced and extending ramps on one of said flange faces and said cam follower including a pair of projections along the other of said flange faces circumferentially spaced one from the other through an angle of about 180° for engagement along respective ones of said ramps, whereby said projections lie in sliding engagement with said ramps in response to relative rotation between said adaptor and said member, one of said flanges lying in resilient yielding engagement with the other of said flanges at the point of engagement between said projections and said ramps.

17. Apparatus according to claim 16 wherein said second rotating means includes a generally cylindrical member disposed on said sleeve, said cylindrical member having a pair of radially extending, diametrically opposed elements to facilitate manual purchase of said cylindrical member and rotation thereof about said sleeve, said projections being located on the flange on said member and said pair of radially extending elements being located on the opposite side of the flange on said member and at locations spaced circumferentially from said projections, the flange on said member being resilient and yieldable when said projections engage along said ramps.

18. Apparatus according to claim 16 wherein said ramps are separated one from the other by end stops, said projections engaging said end stops to rotate said adaptor in response to rotation of said cylindrical member in the opposite direction.

19. Apparatus according to claim 16 wherein said adapter and said second means are formed solely of plastic material thereby facilitating their one-time disposable use.

* * * * *